United States Patent
Knafel et al.

(10) Patent No.: US 10,197,584 B2
(45) Date of Patent: Feb. 5, 2019

(54) ANALYSIS SYSTEM FOR ANALYZING BIOLOGICAL SAMPLES

(75) Inventors: Andrzej Knafel, Walchwil (CH); Joerg Haechler, Oberwil b. Zug (CH)

(73) Assignee: Roche Diagnostics Operations, Inc., Indianapolis, IN (US)

(*) Notice: Subject to any disclaimer, the term of this patent is extended or adjusted under 35 U.S.C. 154(b) by 378 days.

(21) Appl. No.: 13/288,416

(22) Filed: Nov. 3, 2011

(65) Prior Publication Data

US 2012/0109531 A1     May 3, 2012

(30) Foreign Application Priority Data

Nov. 3, 2010 (EP) .................................. 10189758

(51) Int. Cl.
| | |
|---|---|
| *G01N 33/48* | (2006.01) |
| *G01N 35/00* | (2006.01) |
| *G05B 19/418* | (2006.01) |
| *G06G 7/58* | (2006.01) |
| *G01N 35/04* | (2006.01) |

(52) U.S. Cl.
CPC ... *G01N 35/00871* (2013.01); *G01N 35/0092* (2013.01); *G05B 19/41865* (2013.01); *G01N 2035/0094* (2013.01); *G01N 2035/00881* (2013.01); *G01N 2035/047* (2013.01); *Y02P 90/20* (2015.11)

(58) Field of Classification Search
CPC .... G06F 10/366; G06F 10/3412; C12M 41/48
See application file for complete search history.

(56) References Cited

U.S. PATENT DOCUMENTS

| | | |
|---|---|---|
| 6,581,012 B1 | 6/2003 | Aryev et al. |
| 6,599,749 B1 | 7/2003 | Kodama et al. |
| 7,010,760 B2 | 3/2006 | Arnstein et al. |
| 7,379,821 B2* | 5/2008 | Yung et al. ..................... 702/19 |
| 2002/0147515 A1 | 10/2002 | Fava et al. |
| 2007/0196909 A1* | 8/2007 | Showalter et al. ........ 435/283.1 |
| 2007/0282476 A1 | 12/2007 | Song et al. |
| 2008/0113440 A1 | 5/2008 | Gurney et al. |
| 2008/0235055 A1 | 9/2008 | Mattingly et al. |
| 2009/0247417 A1 | 10/2009 | Haas et al. |

FOREIGN PATENT DOCUMENTS

| | | |
|---|---|---|
| EP | 0 596 205 A2 | 5/1994 |
| EP | 0 795 754 B1 | 12/2004 |
| EP | 0 902 290 B1 | 11/2008 |
| EP | 1 248 170 B1 | 9/2009 |
| WO | 94/11838 A1 | 5/1994 |

\* cited by examiner

*Primary Examiner* — Eric S Dejong

(74) *Attorney, Agent, or Firm* — Dinsmore & Shohl LLP

(57) ABSTRACT

An analysis system for analyzing biological samples is disclosed, and which may comprise two or more analysis system components for performing an analysis. A sample workflow manager and an instrument manager coupled to the sample workflow manager may be coupled to the system components for receiving a process status from the system components, wherein the sample workflow manager provides at least one preconfigured processing route to the instrument manager in accordance with the process status. The instrument manager may comprise a memory for storing the preconfigured processing route, wherein the instrument manager is adapted for receiving a test order for analyzing the biological sample using the system components, and wherein the instrument manager is adapted for generating commands for controlling a transport device for transporting the biological sample in accordance with the test order and the at least one preconfigured processing route.

19 Claims, 7 Drawing Sheets

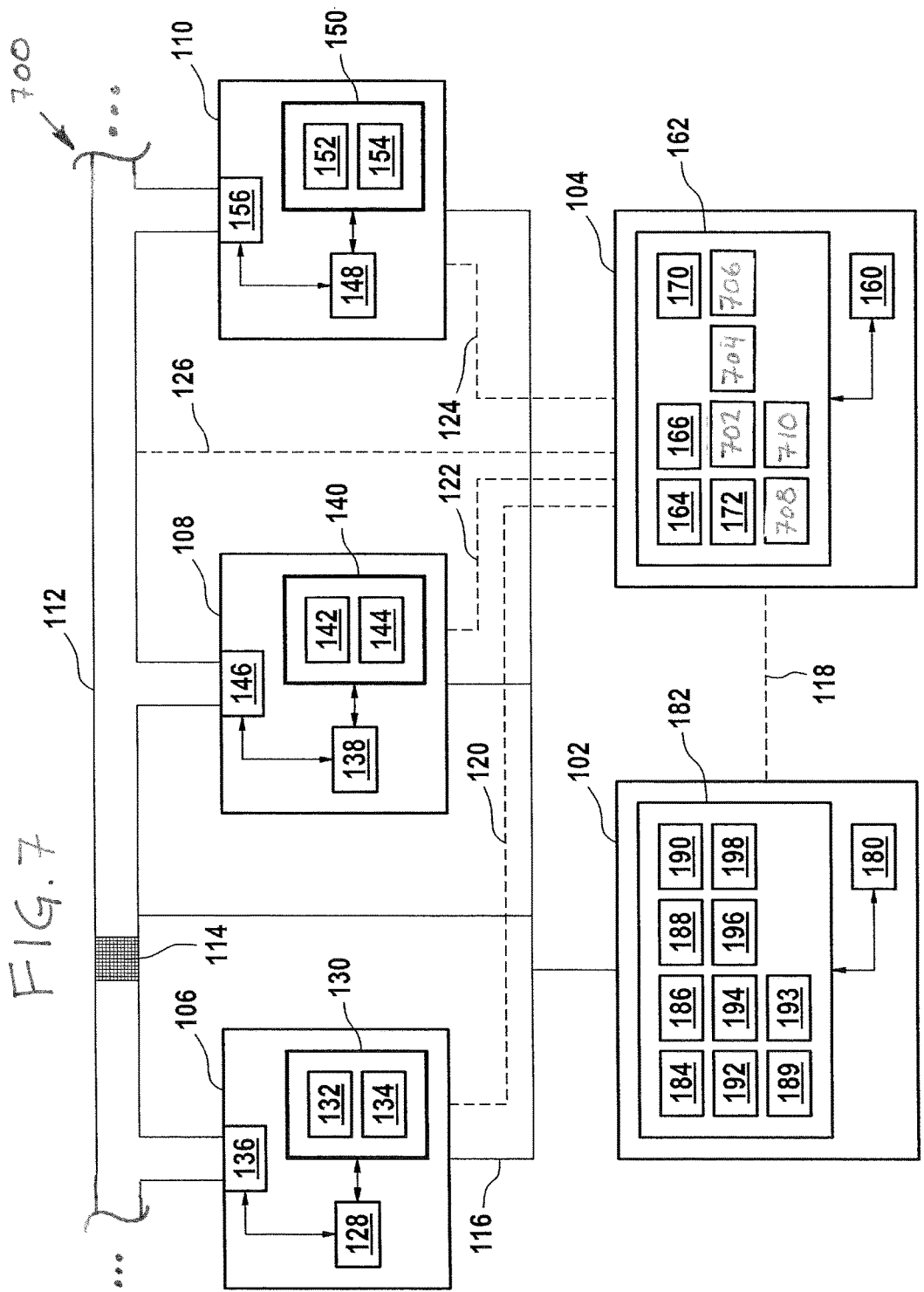

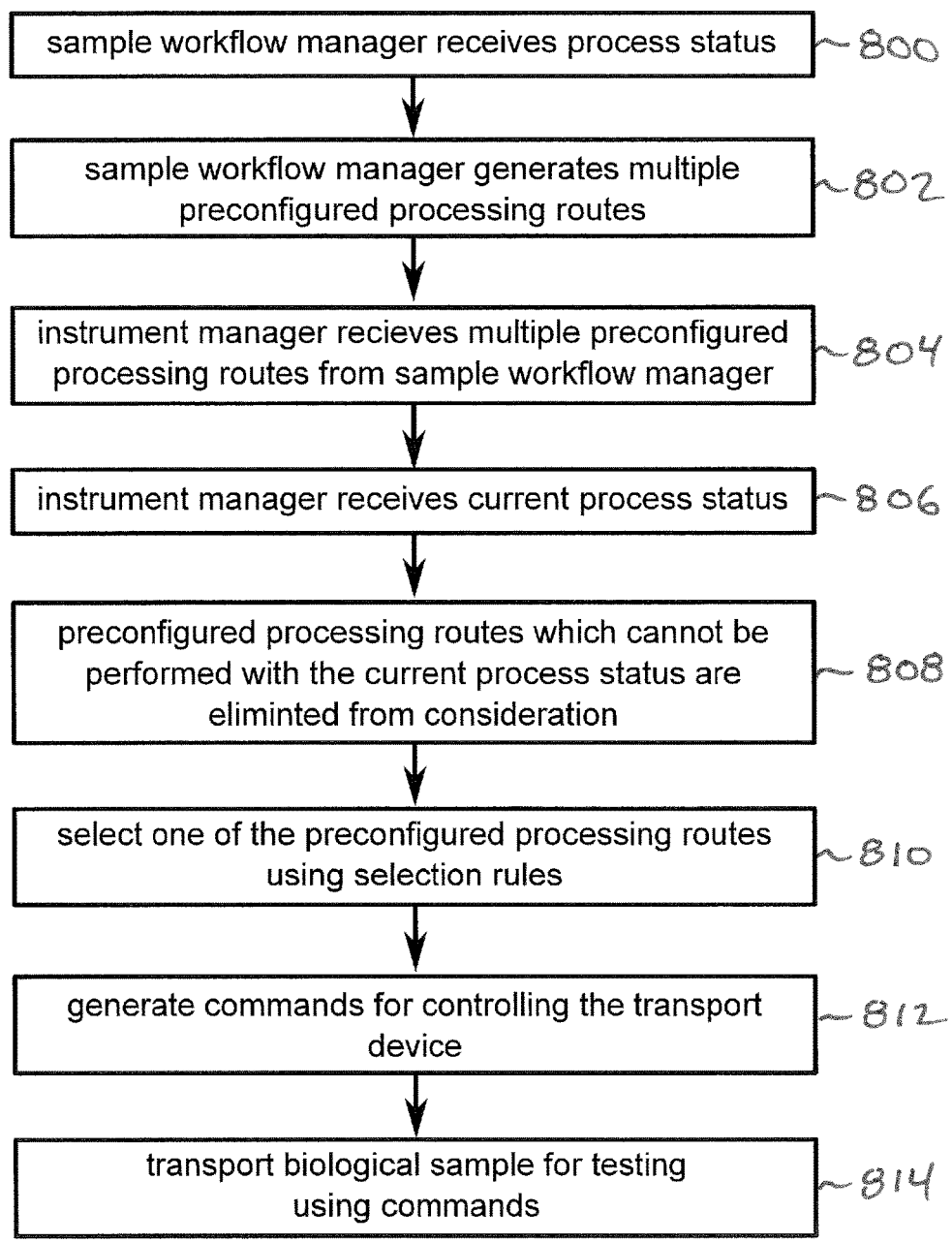

ANALYSIS SYSTEM FOR ANALYZING BIOLOGICAL SAMPLES

CROSS-REFERENCE TO RELATED APPLICATIONS

This application claims the benefit of priority under 35 U.S.C. § 119 of European Application No. 10 189 758.5, filed Nov. 3, 2010.

TECHNICAL FIELD

The disclosed embodiments relate to an analysis system for analyzing biological samples, in particular an analysis system with a sample workflow manager.

BACKGROUND

In analytical laboratories, in particular clinical laboratories, a multitude of analyses on biological samples are executed in order to determine physiological and biochemical states of patients being indicative of a disease, nutrition habits, drug effectiveness or organ function.

Biological samples used in those analyses can be a number of different biological fluids such as blood, urine, cerebral-spinal fluid, saliva etc. These original biological samples may further be aliquoted or divided into multiple biological samples.

Modern clinical laboratories may use networks of analytical devices to automatically analyze biological samples.

Disadvantages of the current automated systems for analyzing biological samples include that there are real-time dependencies among analytical devices or subsystems of the laboratory automated system and that there may be single point-of-failure dependencies.

SUMMARY

An analysis system for analyzing biological samples is disclosed. The analysis system may comprise at least first and second analysis system components for performing an analysis, wherein a first component comprises a transport device; and a second component comprises at least one of a pre-analytic device, an analyzer and a post-analytic device for characterizing a property of a biological sample; and a sample workflow manager and an instrument manager coupled to the sample workflow manager, wherein the sample workflow manager is coupled to the at least first and second analysis system components for receiving a process status from the at least first and second analysis system components, wherein the sample workflow manager provides at least one preconfigured processing route to the instrument manager in accordance with the process status; wherein the instrument manager is coupled to the transport device; wherein the instrument manager comprises a memory for storing the at least one preconfigured processing route, wherein the instrument manager is adapted for receiving a test order for analyzing the biological sample using the second analysis system components, wherein the instrument manager is adapted for generating commands for controlling the transport device for transporting the biological sample to the second analysis system component in accordance with the test order and the at least one preconfigured processing route.

BRIEF DESCRIPTION OF THE DRAWINGS

FIG. 7 illustrates an analysis system according to one or more embodiments shown and described herein; and FIG. 8 shows a flow chart which illustrates a method according to one or more embodiments shown and described herein.

Figure 1:
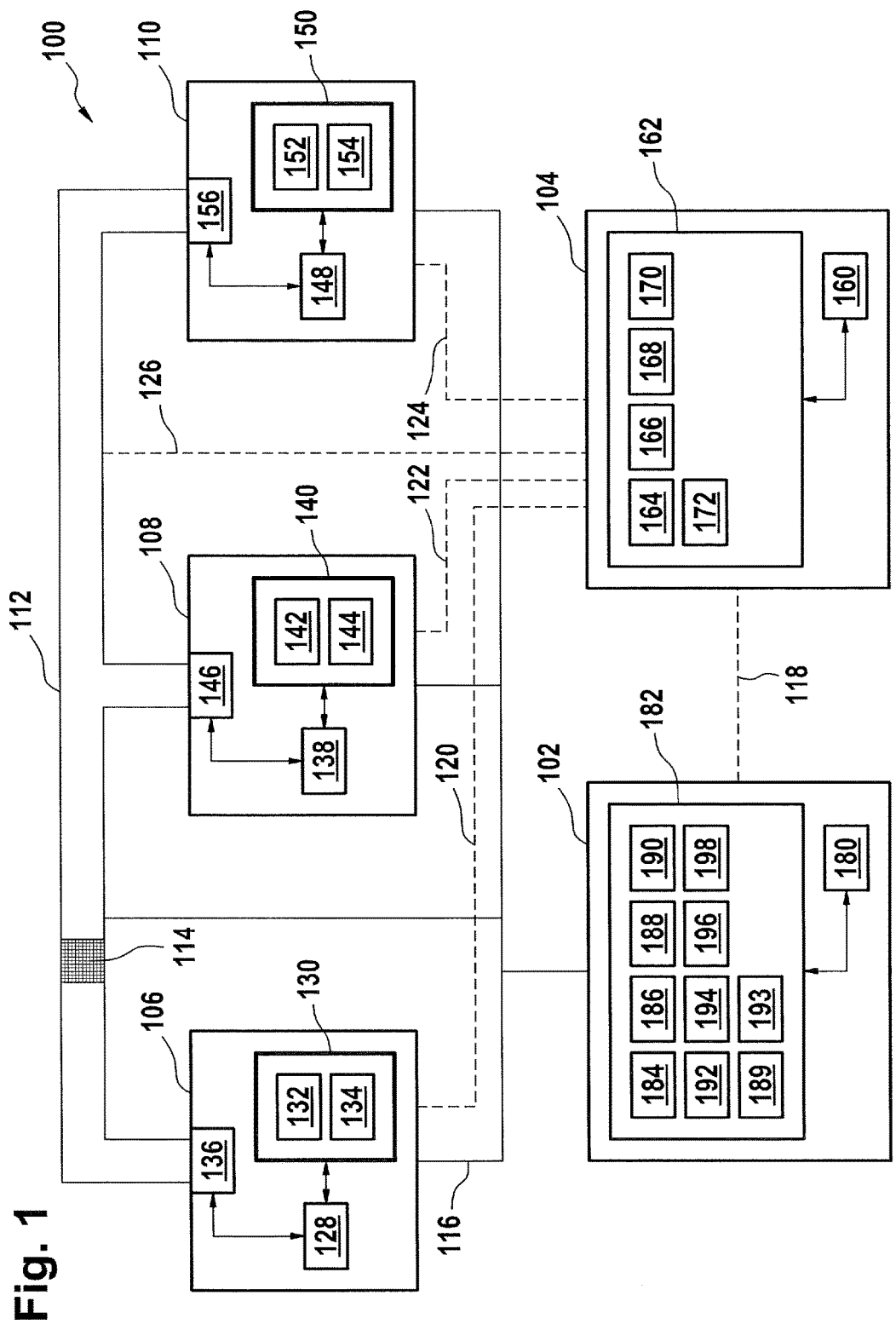
FIG. 1 illustrates an analysis system according to one or more embodiments shown and described herein.

LIST OF REFERENCE NUMERALS 100 analysis system
102 sample workflow manager
104 instrument manager
106 second analytical device
108 third analytical device
110 fourth analytical device
112 first analytical device or conveyor line
114 biological sample
116 network
118 communication link between instrument manager and sample workflow manager
120 communication link between instrument manager and first analytical device
122 communication link between instrument manager and second analytical device
124 communication link between instrument manager and third analytical device
126 communication link between instrument manager and conveyor line
128 processor
130 computer-readable storage medium
132 program
134 instructions
136 pre-analytic device
138 processor
140 computer-readable storage medium
142 program
144 instructions
146 analyzer
148 processor
150 computer-readable storage medium
152 program
154 instructions
156 post-analytic device
160 processor
162 computer-readable storage medium
164 program
166 test order
168 preconfigured process route
170 command generation module
172 sample tracking message
180 processor
182 computer-readable storage medium
184 program
186 process route database
188 process route creation module
189 process status 190 process route update module
192 rule set
193 updated process status
194 query
196 query response module
198 query response
200 analysis system
202 sample workflow manager
204 sets of possible workflows
206 rules for adjustment of workflow sets
208 sends current workflow set to instrument manager
210 instrument manager
212 current set of workflows
214 conveyor line
216 conveyor switching unit
218 sample 45
220 sample tracking message
222 instructions
224 route 1
226 route 2
228 analytical device
230 process status
500 analysis system
502 sample workflow manager
504 pre-configured processing route
506 instrument manager
508 control commands
510 pre-analytic apparatus
512 transport device
514 analyzer
516 test order
518 device status
520 set of pre analytic devices
522 set of analytical devices
600 laboratory information system
602 middle ware system
604 sample workflow manager
606 first scenario
608 pre-analytic apparatus
610 instrument manager
612 transport device
614 analyzer
616 instrument manager
618 instrument manager
700 analysis system
702 current process status
704 preconfigured processing routes
706 selection rules
708 route selection module
710 selected preconfigured processing route

DETAILED DESCRIPTION

Various embodiments of the present disclosure describe a system architecture and communication structure allowing dynamic management of the sample across pre-analytics, analytics and post-analytic platforms or analytical devices. The management of the samples may allow for dynamic routing, aliquoting, sorting and buffering of samples depending on the status of the analyzer, the available tests on the analyzer (status of test), the workload, and other relevant status information from interacting systems.

The architecture shows an Instrument Manager (IM) in connection with the pre-analytical system as well as a Sample Workflow Manager (SWM). In accordance with the status information received from the connected systems the SWM may define valid routes the samples could take and the criteria needed to decide what route to be assigned to a specific sample in accordance with processing orders, and container/specimen characteristics.

Both the available routes as well as the criteria to select the routes are downloaded to the IM. The IM works with the actual configuration as long as no updated information is received from the SWM.

In situations in which the SWM is not working, the IM will continue working with the actual configuration. This may lead to a suboptimal management of the samples but does not prevent the system from processing the majority of the samples successfully.

Embodiments of the disclosure may include the avoidance of real-time dependences among subsystems of the Laboratory Automation System; the minimization of single-point-of-failure dependences wherein the Dynamic Workflow management may be viewed as an optimization, specifically, processing subsystems may be able to function without management subsystems. For example, with some default workflows; and decoupling of the subsystems which means development and testing of the subsystems against interfaces and minimizing the need for testing of the entire system.

One embodiment described herein provides for an analysis system for analyzing biological samples. Biological samples as used herein encompass matter or material which contains matter that is originally of biological origin. The biological sample may be material entirely taken from an organism or it may be matter which is taken from an organism and processed by mixing with other material. For instance a blood or urine sample may be mixed with a preservative, a solvent or diluted. The biological sample also encompasses biological material which has been broken down or processed with chemicals such as enzymes or other materials for changing the chemical structure of the biological sample.

The analysis system comprises two or more analysis system components for performing an analysis. An analysis system component as used herein encompasses any device which is used for or contributes to the processing or analyzing a biological sample. An analysis system component is a component of an analysis system which is used for either analyzing a biological sample or performs a contribution to the analysis of the biological sample. For instance, an analysis system component may be an analyzer, a pre-analytical device, and a post-analytic device (such analysis system components may also be referred to by the term analytical device). An analysis system component may be considered to be an element or component of an analysis system which contributes to the functioning of an analysis system, such as, the transport device or conveyor line.

An analytical device may be an analyzer for measuring a physical property of the biological sample, such as a pre-analytical device, an analyzer and a post-analytical device. An analytical device may also be a device for detecting the presence of certain biological materials within the biological sample. An analytical device further may be a device which performs a transformation or action on a biological sample. For instance, an analytical device may perform pipetting or may add chemicals or otherwise process the biological sample.

At least one of the analysis system components may be an analyzer for characterizing a property of a biological sample. As mentioned previously, an analyzer as used herein is an analytical device which performs a measurement which may be used to characterize a property of the biological sample. The biological sample may be probed with electromagnetic radiation or the biological sample may be exposed to other chemicals which cause a reaction if the biological sample has certain properties or compositions.

At least one of the analysis system components may also be a pre-analytic apparatus. As used herein, a pre-analytic apparatus is an apparatus which performs an operation on or a transformation of the biological sample. For example, a pre-analytic device may open a biological sample, or perform a transformation such as adding a solvent or material for diluting a biological sample. Examples of operations performed by pre-analytic devices include, but are not limited to: centrifugation, decapping, transportation, recapping, sorting, and aliquoting. During an operation performed by a pre-analytic apparatus, there may be a transformation of the biological sample. For example, a reagent may be added to the biological sample. The transformation of the biological sample by a pre-analytic apparatus may be for the preparation of a sample to facilitate or enable analysis of the sample by an analyzer.

At least one of the analysis system components may be a transport device for transporting a biological sample between physical locations or between different analytical devices. A transport device may be, but is not limited to, a conveyor system or a robotic arm. A transport device contributes to the analysis of a biological system by integrating distinct analytical devices. In some examples a transport device may be integrated with a pre-analytic apparatus or an analyzer.

The analysis system further comprises a sample workflow manager and an instrument manager coupled to the sample workflow manager. An instrument manager may be a computer or a control system connected to two or more analysis system components and controls the function of the two or more analysis system components. In some embodiments at least one of the analysis system components may be a transport device. In further embodiments, the instrument manager may control multiple analysis system components in addition to the transport device. The multiple analysis system components may be any combination of pre-analytic devices, post-analytic devices and analyzers.

In yet a further embodiment, the instrument manager may control the two or more analysis system components. In other embodiments, the instrument manager communicates with controllers which are embedded, onboard or otherwise integrated with the two or more analysis system components. In this embodiment, the instrument manager sends commands or communicates with the two or more analysis system components.

A sample workflow manager encompasses a computer or a control system which sends commands or instructions to the instrument manager. The sample workflow manager determines preconfigured processing routes for use by the instrument manager for controlling the two or more analysis system components. For example, one of the analysis system components may be a transport device. In some embodiments, the preconfigured processing routes may be a set of commands which instruct the transport device to move a sample between a sequence of pre-analytic devices, post-analytic devices and analyzers.

The sample workflow manager is coupled to the two or more analysis system components for receiving a process status from the two or more analysis system components. A process status may be data which is descriptive of the current availability or status of each of the two or more analysis system components. The process status can therefore be used for planning or controlling the workflow of the biological sample as it is being analyzed by the analysis system. The sample workflow manager provides at least one pre-configured processing route to the instrument manager in accordance with the process status. A processing route may be a set of commands or instructions that the instrument manager uses for completing workflow of a biological sample in the analysis system.

In the analysis system, the planning of the workflow and the actual implementation is divided into two separate components; the sample workflow manager and the instrument manager. The sample workflow manager plans the workflow on a higher level, and the instrument manager implements or controls the two or more analysis system components to perform the analysis. For example, if one of the analysis system components is a transport device, the sample workflow manager may plan the workflow by specifying a set of targets which is descriptive of a sequence of analysis system components. The instrument manager may then implement the workflow by controlling the transport device such that the biological sample is transported according to the sequence of analysis system components specified by the set of targets.

It is to be appreciated that if the sample workflow manager loses connection with the analysis system components and/or the instrument manager then the analysis system will continue to process the biological sample. This is due to the workflow manager having the preconfigured processing route once the processing of a biological sample begins. In yet a further embodiment, the analysis system's workflow management and the instrument management is divided wherein the instrument manager will not become overloaded or over-flooded with data from the two or more analysis system components.

The sample workflow manager receives the process status from the two or more analysis system components and generates or retrieves from a database at least one preconfigured processing route that is provided to the instrument manager. Based on the preconfigured processing route, the instrument manager controls the two or more analysis system components to process or analyze the biological sample. At least one of the analysis system components may, for example, be a transport device. The at least one preconfigured processing route may be a sequence of analysis system components to which the transport device transports the biological sample.

The instrument manager is coupled to the at least two or more analysis system components. The instrument manager comprises a memory for storing the at least one preconfigured processing route. The instrument manager may be adapted for receiving a test order for analyzing the biological sample using the analyzer. The instrument manager may also be adapted for generating commands for controlling the transport of the biological sample to the analyzer in accordance with the test order and the at least one preconfigured processing route.

In another embodiment, the sample workflow manager provides a single pre-configured processing route for the biological sample. At least one of the analysis system components may be a pre-analytical apparatus for performing pre-analytic operations on the biological sample. In another embodiment, a transport device and the pre-analytic apparatus may be integrated into a single unit. In yet a further embodiment, the pre-analytic apparatus is separate from the transport device and the analyzer. The sample workflow manager may provide the single pre-configured processing route before the pre-analytic apparatus has finished performing the pre-analytic operations on the biological sample.

In another embodiment, a transport device comprises at least one conveyor line adapted for moving a sample holder containing the biological sample between two or more analysis system components. In this embodiment, the transport device is an analysis system component. In another embodiment, the conveyor line is adapted for moving multiple sample holders each of which contain a biological sample between other analysis system components. The pre-configured processing route comprises a set of targets. The set of targets is descriptive of a sequence of the analysis system components. The set of targets specify the order of the analysis system components to which a sample holder or the biological sample within it is delivered to. In a further embodiment, the set of targets only specify the sequence of analysis system components to which the biological sample is delivered to. Once the biological sample reaches an analysis system component, the analysis system component may receive detailed instructions on how to process the biological sample either from a laboratory information system or from a middleware program which manages data from the laboratory information system, or both.

The sequence of analysis system components may be chosen from the analysis system components. The instrument manager provides the at least one conveyor line with conveyance instructions for conveying the biological sample to the sequence of analysis system components in accordance with the set of targets.

In another embodiment, the pre-configured processing route comprises at least one conditional statement. The at least one conditional statement provides at least one alternative target to be substituted into the set of targets. The instrument manager may be adapted for receiving the process status. The instrument manager may also be adapted for modifying the conveyance instructions in accordance with the process status and the at least one conditional statement. Therefore, if a particular analysis system component is not functioning or is too busy the conditional statement can be used for further processing of the biological sample without using the analysis system component that is not available. Minimal processing time and monitoring of the biological sample is extremely minimal due to the conditional statement.

In another embodiment, the pre-analytic apparatus is an aliquoting device for aliquoting the biological sample. In the process of aliquoting, the biological sample may be divided into equivalent biological samples. For example, during the aliquotation process the biological sample may be divided into multiple biological samples and each of the derivative or child biological samples may have individual targets which send the biological samples to a particular analytical device.

The analysis system may be adapted for first processing the biological sample using the pre-analytic apparatus. The analysis system may further be adapted for receiving the single pre-configured processing route before aliquoting the biological sample. The analysis system is further adapted for aliquoting the biological sample before conveying the biological sample to the sequence of analysis system components. References to the biological sample in this context it is understood that biological sample may refer to the group of aliquoted biological samples. Each of the derivative biological samples may also be routed separately to different analysis system components.

In another embodiment, the two or more analysis system components receive test orders for performing analysis from a laboratory information system. In this embodiment, the biological sample or samples are sent to the analytical devices using the set of targets. Once a biological sample reaches an analytical device, the analytical device receives the test order directly from the laboratory information system.

In another embodiment, the sample workflow manager may be adapted for repeatedly receiving an updated process status from the two or more analysis system components. The updated process status encompasses data which is descriptive of the current process status of the two or more analysis system components. As the biological sample is being analyzed the process status of various components of the analysis system may change. For example, at least one of the analysis system components may have a malfunction or need service by an operator. Additional biological samples may also be placed in the analysis system for analysis, in which case, in some instances it may be beneficial to change a preconfigured processing route such that biological samples are processing more efficiently. The updated processing status comprises data that would be descriptive of such situations. The at least one preconfigured processing route is updated repeatedly in accordance with the updated processing status. The sample workflow manager is adapted for providing the updated at least one preconfigured processing route to the instrument manager. This embodiment allows the at least one preconfigured processing route to be adjusted to use the analysis system more efficiently. In further embodiments, the sample workflow manager may select the updated at least one preconfigured processing route from a database. In yet further embodiments, a software module may be used to modify the at least one preconfigured processing route.

In another embodiment, the sample workflow manager further comprises a rule set containing rules for adjusting the at least one preconfigured processing route in accordance with the updated process status. The sample workflow manager is adapted for updating the at least one preconfigured processing route in accordance with at least the rule set and the updated processing status. The rule set as used herein comprises instructions or computer code which may be used for adjusting the at least one preconfigured processing route. For example, if an analysis system component is non-functional there may be rules about which other analysis system component to route a biological sample to perform the same function. There may also be rules which give certain biological samples priority over other biological samples. There may also be rules which control an optimization process for reducing the overall time for analyzing all of the biological samples.

In another embodiment, at least one of the analysis system components may be a pre-analytic apparatus for performing pre-analytic operations on the biological sample. The instrument manager may be adapted for generating commands for controlling the operation of the at least one pre-analytic apparatus in accordance with the at least one preconfigured processing route.

In another embodiment, at least one of the analysis system components may be a post-analytic apparatus for performing post-analytic operations on the biological sample. The instrument manager is adapted for generating commands for controlling the operation of the at least one pre-analytic apparatus in accordance with the at least one preconfigured processing route. A post-analytic apparatus may be an apparatus which does not perform a measurement on a biological sample but performs some operation on the biological sample after a measurement has been performed. For example, a post-analytic apparatus may already cap a biological sample for storage. The post-analytic apparatus may also perform a transformation on a biological sample.

In another embodiment, the instrument manager may be adapted for receiving sample tracking messages from the two or more analysis system components. Sample tracking messages encompass data which is descriptive of the physical location and/or the processing status of a biological sample. For example, a sample tracking message may identify the location of a biological sample as being within or being processed by an analytical device. A tracking message may also be the identification of a biological sample as being in transit or being transported between the analysis system components. For example, the tracking message may identify the location of the biological sample on a conveyor or conveyance system. The instrument manager is able to update or change the commands for controlling the transport of the biological sample based on its status within an analysis system component or its physical location.

In another embodiment, the instrument manager may be adapted for sending a query to the sample workflow manager. The query is a request for instructions on how to process the biological sample using the two or more analysis system components. The sample workflow manager may be adapted for constructing a query response in accordance with the query. The sample workflow manager may be adapted for sending the query response to the instrument manager. The instrument manager may be adapted for providing commands to the two or more analysis system components in accordance with the query response. In some embodiments the instrument manager may send a query when there is some error or failure which does not allow the preconfigured processing route to be followed for a particular biological sample. A query may be also sent if a predetermined set of conditions is met or exceeded, for example, if a large number of biological samples is added for processing after the processing of the biological sample has been started. A query may also be triggered by a message from an analysis system component to the instrument manager or by an analysis of data from an analysis system component by the instrument manager. For example, if some biological property of the biological sample is measured and is outside of an acceptable range, a query may be sent.

In a further embodiment, the analysis system may characterize multiple biological samples. In another embodiment, the preconfigured processing route may contain instructions for processing multiple biological samples simultaneously.

In another embodiment, the analysis system further comprises at least one conveyor line adapted for moving sample holders each containing one of the multiple biological samples between the two or more analysis system components. A conveyor line, as used herein, encompasses a system for conveying a biological sample between the two or more analysis system components.

In another embodiment, the instrument manager may be adapted for controlling the movement of the sample holders using the conveyor line using commands generated in accordance with at least one preconfigured processing route.

In another embodiment the sample workflow manager may provide multiple preconfigured processing routes to the instrument manager in accordance with the process status. The sample workflow manager may provide preconfigured processing routes for commonly or pre-specified types of samples. The sample workflow manager may also provide preconfigured processing routes for previously used types of test orders. The instrument manager may be configured for selecting one of the multiple preconfigured processing routes in accordance with the test order. For example, the instrument manager may select a preconfigured processing route which routes the biological sample to a sequence of analysis system components which are able to perform all the tests specified in the test order.

The instrument manager may be further configured to use the one of the multiple preconfigured processing routes to generate the commands for controlling the transport device for transporting the biological sample. In this embodiment, the instrument manager may contain a number of preconfigured processing routes. The instrument manager itself may be able to select a preconfigured processing route which will satisfy the test order. Therefore, the instrument manager is able to successfully process the received test orders when the sample workflow manager is not functioning.

In another embodiment, the instrument manager may be configured for selecting the one of the multiple preconfigured processing routes such that all tasks requested by the test order are satisfied. In this embodiment, the instrument manager may be able to independently select the preconfigured processing route used to generate the commands.

In another embodiment, the instrument manager may be configured for receiving the process status. In some instances the process status that the instrument manager receives is an updated or current process status. For example, the process status may be different than the process status when the sample workflow manager generated the multiple preconfigured processing routes. The instrument manager may be configured to select the one of the multiple preconfigured processing routes by determining which of the multiple preconfigured processing routes is allowed by the process status. In this embodiment, the status of the analysis system may be different when the sample workflow manager generated the multiple preconfigured processing routes and when the instrument manager begins to transport a biological sample. For instance, since the sample workflow manager generated the preconfigured processing routes a particular analysis system component may malfunction. Using an updated or current process status may enable the analysis system to function better.

In another embodiment, the instrument manager may be configured to select the one of the multiple preconfigured processing routes at least partially in accordance with a selection rule set. In this embodiment, predetermined rules can be used to select which of the multiple preconfigured processing routes is used to transport the biological sample.

The rules used to select the preconfigured processing route may assign a priority to each rule. For instance more than one preconfigured processing route may be allowed by the selection rule set. Assigning a priority to the selection rules enables the proper preconfigured processing route to be selected. For example, routes "A" and "B" may both satisfy a first rule, "A" may satisfy a second rule, and "B" may satisfy a third rule. If the second rule has a higher priority than the third rule then route "A" is used.

The rules may select routes based on different levels of importance. Some rules may specify a particular order of analysis system component to ensure that cross-contamination does not occur. Rules may also specify operations such that an aliquotation is performed.

Rules may also be used which sacred increase the efficiency or speed at which orders are produced. Rules may also specify analysis system components with a lower workload to be selected. Such rules could be used to reduce the number of analysis system components which are used.

Rules can also be used to increase the confidence of a measurement. Rules may sometimes specify that when a sample is rerun or retested that a particular test is done by the same analysis system component. In some instances the rules may specify that when a sample is rerun or retested that a particular test is done by a different analysis system component in order to compare the results.

Embodiments of the present disclosure are described in detail hereafter with reference to the attached drawings.

FIG. 1 illustrates an analysis system 100 according to an embodiment of the present disclosure. Shown in FIG. 1 there is a sample workflow manager 102, an instrument manager 104, a first analysis system component 112, a second analysis system component 106, a third analysis system component 108, and a fourth 110. The first analysis system component is a conveyor line 112 for moving or conveying a biological sample 114 between the second, third, and fourth analysis system components 106, 108, 110. Shown in this embodiment there is a network 116 which connects the computers or control devices of the sample workflow manager 102 and the second analysis system component 106, the third analysis system component 108, and the fourth analysis system component 110. In some embodiments the conveyor line 112 is also connected to the sample workflow manager 102 via the network 116. The network 116 is any computer network or communications system which allows the second, third, and fourth analysis system component 106, 108, 110 and the conveyor line 112 to send a process status to the sample workflow manager 102.

In addition there is a communication link 118 between the sample workflow manager and the instrument manager. The communication link is any suitable networking system or computer communication system which allows two computers or control systems to exchange data and information.

There is also a communication link 120 between the instrument manager 104 and the second analysis system component 106. There is a communication link 122 between the instrument manager 104 and the third analysis system component 108. There is another communication link 124 between the instrument manager 104 and the fourth analysis system component 110. Also shown is a communication link 126 between the instrument manager 104 and the conveyor line 112. These communication links 118, 120, 122, 124, 126 allow the instrument manager 104 to exchange data and commands with any of these analysis system components the instrument manager 104 is connected to. In some embodiments the network 116 may be identical with the communication links 118, 120, 122, 124, 126. There are however different ways of implementing this. In some alternative embodiments the conveyor line 112 and the second, third, and fourth analysis system components 106, 108, 110 are only connected to the instrument manager 104 on a local network and all network connections from the conveyor line 112 and the second, third, and fourth analysis system components 106, 108, 110 to the sample workflow manager is via the instrument manager 104.

The second analysis system component 106 comprises a pre-analytic device 136. Essentially the second analysis system component 106 is a pre-analytic apparatus. The second analysis system component 106 also comprises a processor 128 connected to the pre-analytic device 136 and a computer-readable storage medium 130. The computer-readable storage medium 130 contains a program 132 which the processor 128 uses to control the operation and functioning of the pre-analytic device 136. The computer-readable storage medium 130 also contains instructions 134 which the second analysis system component 106 receives from the instrument manager 104. The instructions 134 are used by the program 132 to control a pre-analytic operation on the biological sample 114 by the pre-analytic device 136.

The third analysis system component 108 comprises an analyzer 146. The analyzer 146 is for analyzing or measuring a physical property of the biological sample 114. The analyzer 146 is connected to a processor 138 which is connected to a computer-readable storage medium 140. The computer-readable storage medium contains a program 142 and instructions 144 received from the instrument manager 104. The processor 138 uses the program 142 for controlling the operation of the analyzer 146. The instructions 144 are used by the program 142 to generate specific commands to the analyzer 146. The third analysis system component 108 is essentially an analyzer.

The fourth analysis system component 110 comprises a post-analytic device 156. The post-analytic device 156 is connected to a processor 148 which is connected to a computer-readable storage medium 150. The computer-readable storage medium 150 contains a program 152 and instructions 154. The instructions 154 are received from the instrument manager 104. The processor 148 uses the program 152 in accordance with the instructions 154 to control the functioning of the post-analytic device 156 on the biological sample 114.

The instrument manager 104 comprises a processor 160 and a computer-readable storage medium 162. The computer-readable storage medium 162 contains a program 164 which is used to control the operation of the instrument manager 104. The computer-readable storage medium 162 also contains a test order 166 which the instrument manager 104 either received via a network connection, an email, input by an operator or was automatically generated when the biological sample 114 was placed into the analysis system 100. The test order 166 is used by the program 164 to initiate analysis of the biological sample 114 by the analysis system 100. The computer-readable storage medium 162 also contains a preconfigured process route 168. The preconfigured process route 168 may be received from the sample workflow manager 102. The computer-readable storage medium 162 also contains a command generation module 170. The command generation module 170 is computer executable code which uses the preconfigured process route 168 to generate the instructions 134, 144, 154 used by the analysis system components 106, 108, 110. The computer-readable storage medium 162 also contains a sample tracking message 172 which may be received from one of the analysis system components 106, 108, 110, 112. The sample tracking message 172 contains data which indicates the physical location and/or process status of the biological sample 114.

The sample workflow manager 102 comprises a processor 180 and a computer-readable storage medium 182. The computer-readable storage medium 182 contains a program 184 for controlling the operation and function of the sample workflow manager 102. The computer-readable storage medium 182 also contains a process route database 186. The process route database 186 is an optional feature of the sample workflow manager. The process route database 186 contains a database of preconfigured process routes. The computer-readable storage medium 182 also contains a process route creation module 188. The process route creation module 188 is an optional feature of the sample workflow manager 102. The process route creation module 188 is used to generate at least one preconfigured process route 168. The computer-readable storage medium 182 also contains a process status 189. The process status 189 may be used by the program 184 to either select a preconfigured process route from the process route database 186 and/or use the process route creation module 188 to generate the preconfigured process route 168. The computer-readable storage medium 182 also contains a process route update module 190. The process route update module 190 is a rule set 192 to modify the preconfigured process route 168 in accordance with an updated process status 193. The computer-readable storage medium 182 also contains a query 194 received from the instrument manager 104 via the communication link 118. The query 194 contains data with a request for a decision on how to process the biological sample 114. The computer-readable storage medium 182 further contains a query response module 196 which generates a query response 198 in accordance with the query 194. The sample workflow manager 102 then sends the query response 198 to the instrument manager 104. The command generation module 170 of the instrument manager 104 is able to use the query response 198 to generate instructions 134, 144, 154 for operating the analysis system components 106, 108, 110 in accordance with the query 194.

Figure 2:
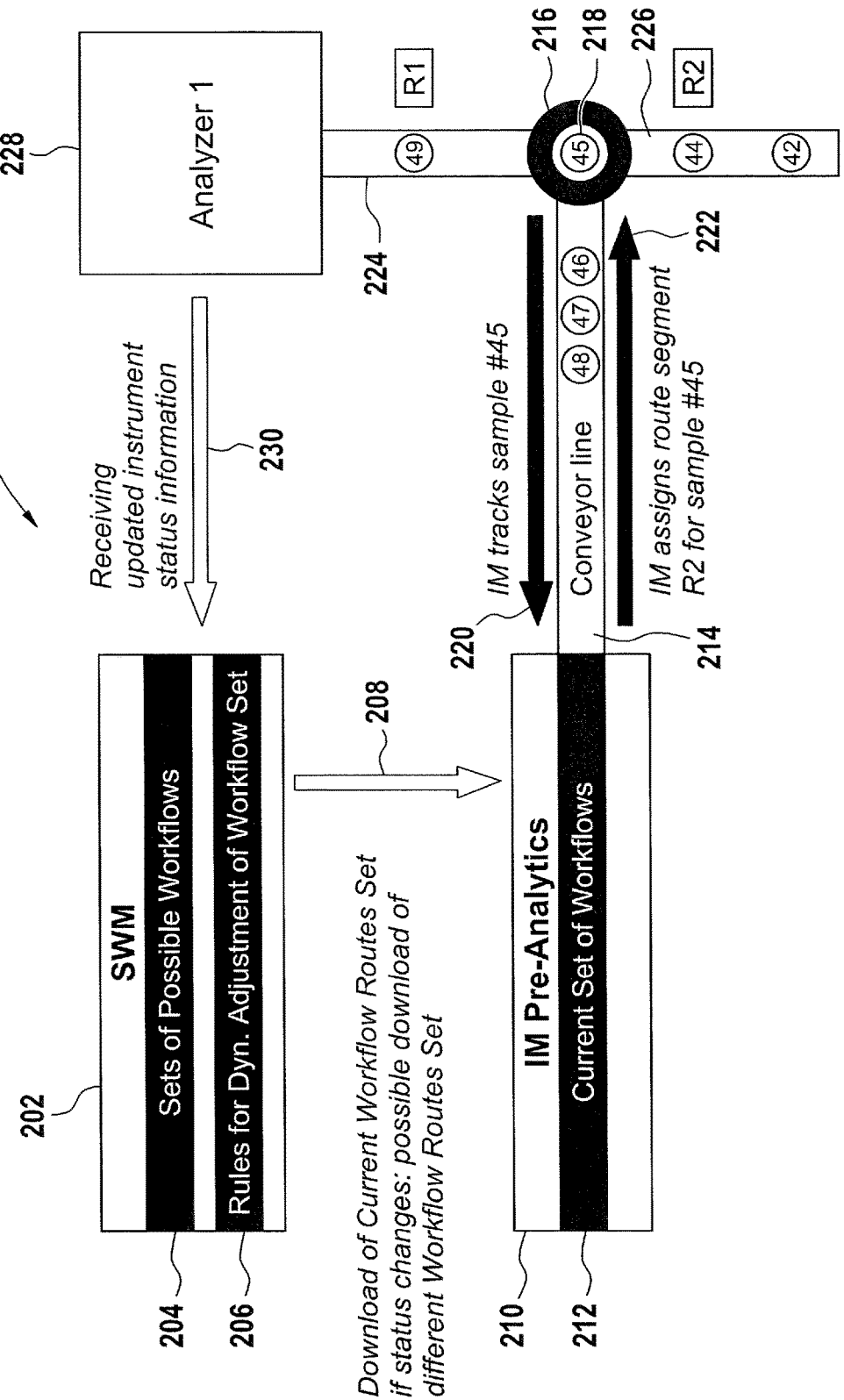
FIG. 2 illustrates an analysis system according to one or more embodiments shown and described herein.

FIG. 2 shows a further embodiment of an analysis system 200 according to an embodiment of the present disclosure. The analysis system 200 in FIG. 2 is illustrated functionally. There is a sample workflow manager 202. The sample workflow manager 202 contains sets of possible workflows 204. This may be considered equivalent to a database of possible workflows. The sample workflow manager 202 also contains rules for adjusting the workflow set 206. The sample workflow manager 202 sends 208 the current workflows to the instrument manager 210. The instrument manager 210 is shown as containing a current set of workflows 212. In this instance the instrument manager 210 is shown as being connected to a conveyor line 214. The conveyor line 214 is a transport device. In this and in some embodiments the instrument manager may function as a pre-analytical device. For example, samples may be loaded into the instrument manager. However, in other embodiments the instrument manager is separate from the analysis system components. The conveyor line 214 is connected to a conveyor switching unit 216. The conveyor switching unit 216 is able to transfer a sample 218 to different conveyor lines. The sample 218, number 45, is located in the conveyor switching unit 216. A decision needs to be made into which route, route number R1. 224 or route number R2, 226, to switch sample 218, number 45. The conveyor switching unit 216 sends a sample tracking message 220 to the instrument manager 210. In accordance with the current set of workflows 212 the instrument manager 210 sends a set of instructions 222 to the conveyor switching unit 216. In this embodiment, the set of instructions 222 assigns sample 218, number 45 to the second route 226. Also connected to route number R1, 224 is an analysis system component 228. The analysis system component is able to send process status data 230 to the sample workflow manager 202. The rules for adjusting the workflow set 206 adjust the sets of possible workflows 204 in accordance with the process status data 230.

Figure 3:
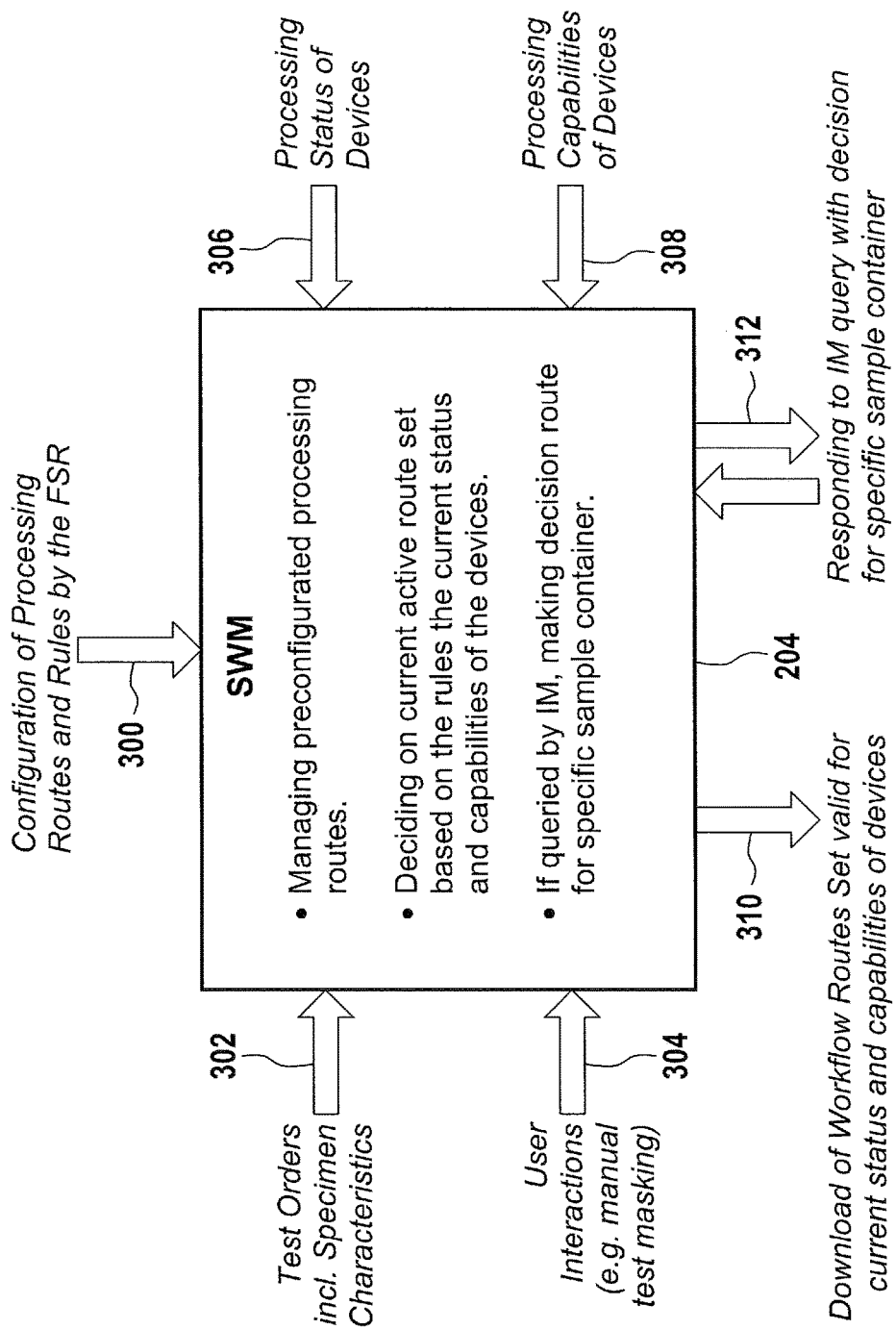
FIG. 3 is a diagram which illustrates the workflow functions of a sample workflow manager according to one or more embodiments shown and described herein.

FIG. 3 is a diagram which illustrates the workflow functions of the sample workflow manager according to a further embodiment of the present disclosure. The sample workflow manager 204 receives a variety of input. Arrow 300 represents the input of processing routes and rules possibly by an operator or downloaded from an external system. Arrow 302 represents the reception of a test order which includes the characteristics of specimens or biological samples which are covered or ordered by the test order. Arrow 304 represents user interactions such as manual test masking or manual control of the analysis system 100. Arrow 306 represents input received in the form of a process status from the analysis system components. Arrow 308 is another message received from the analysis system components which details the processing capabilities of the analytical devices. Using these inputs the sample workflow manager provides several functions, first it manages preconfigured processing routes, it also decides on current active route set based on the rules the current status and capabilities of the devices. This is combined and workflow route sets are sent 310 to the instrument manager 104. In addition the sample workflow manager 204 can respond 312 to instrument manager queries with decisions for specific sample container or biological sample.

Figure 4:
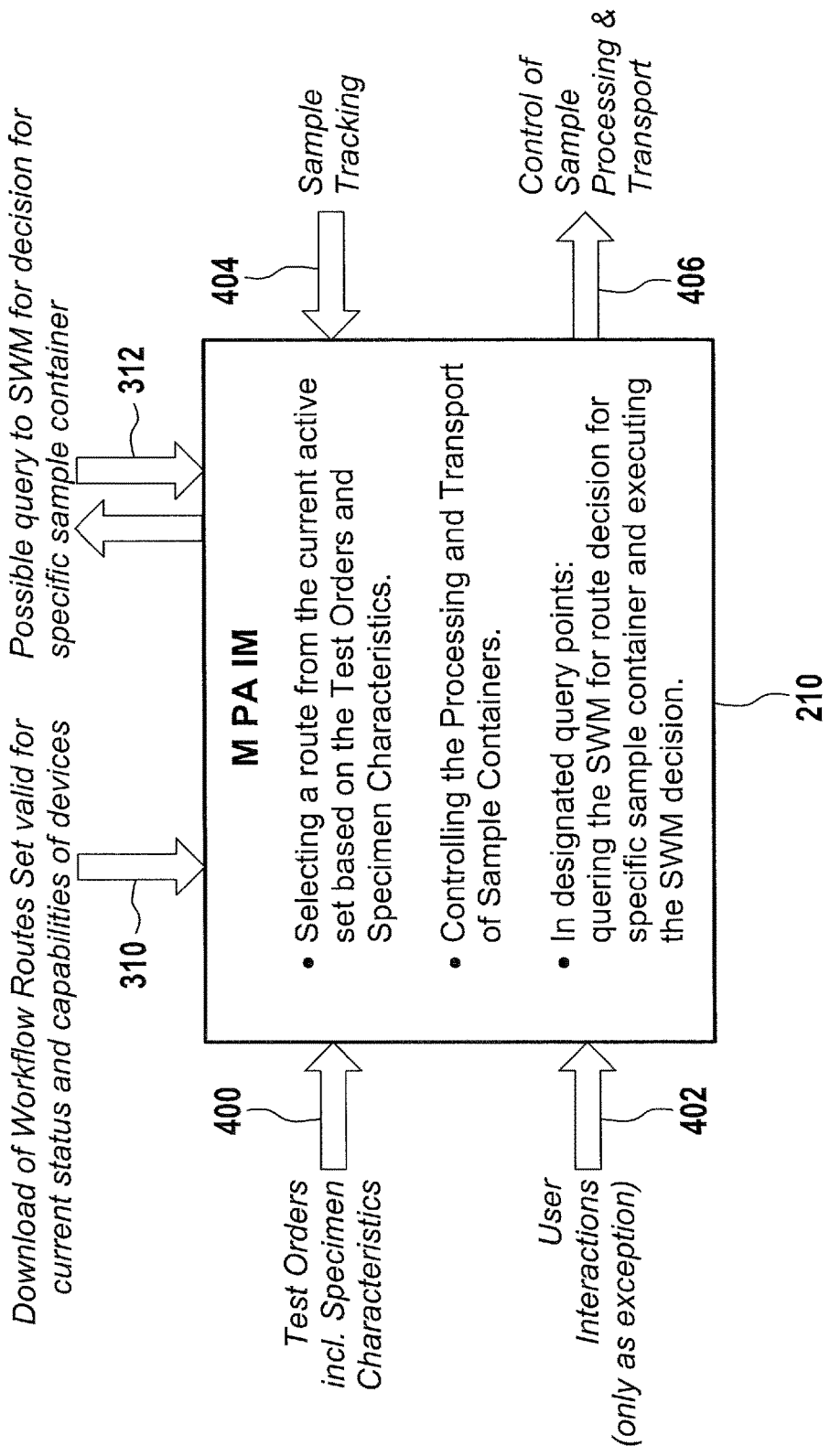
FIG. 4 is a diagram which illustrates the functioning of an instrument manager according to one or more embodiments shown and described herein.

FIG. 4 is a diagram which illustrates the functioning of the instrument manager 210 according to a further embodiment of the present disclosure. The arrow 310 represents the receiving of workflow route sets from the sample workflow manager. The arrows 312 represent queries and reception of a query response from the sample workflow manager. The arrow 400 represents test orders including possibly specimen characteristics. The arrow 402 represents interactions from users, for instance if there is an error or problem that needs to be determined or decided by an operator. The arrow 404 represents sample tracking by the instrument manager. Using these inputs the instrument manager selects a route from the current active set based on the test orders and specimen characteristics. Further, the instrument manager may also control the processing and transport of sample containers. The instrument manager also at designated query points queries the sample workflow manager for route decisions for specific sample containers and executing the sample workflow manager decisions. The arrow 406 represents the sending of instructions or commands for control of sample processing and transport.

Figure 5:
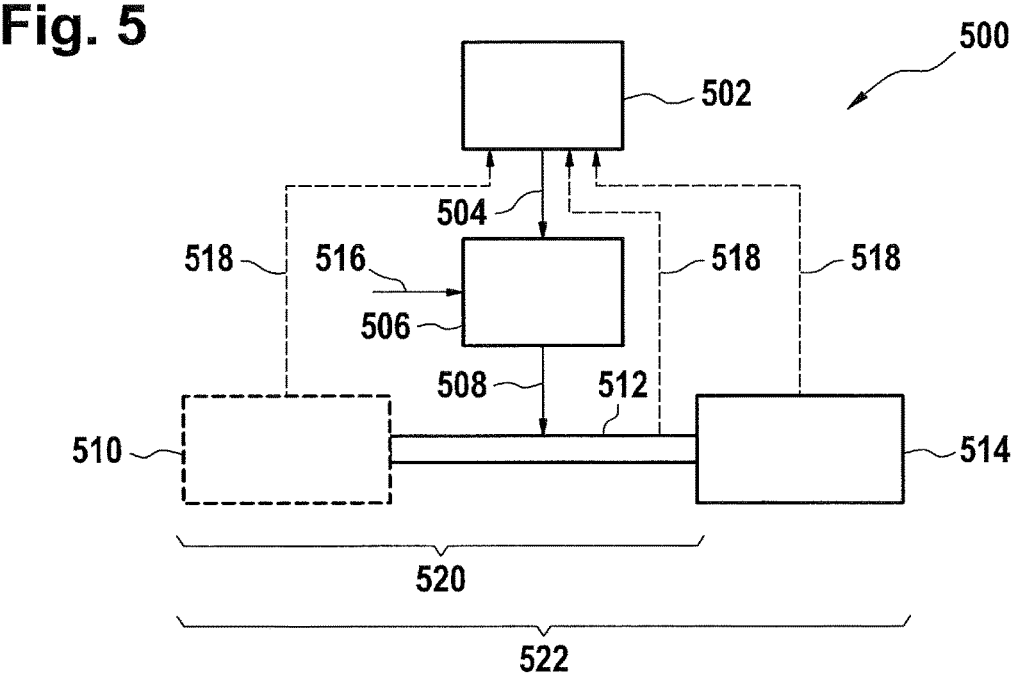
FIG. 5 illustrates an analysis system according to one or more embodiments shown and described herein.

FIG. 5 shows a further embodiment of an analysis system 500 according to a further embodiment of the present disclosure. In this embodiment there is a sample workflow manager 502 which sends a pre-configured processing route 504 to an instrument manager 506. The instrument manager 506 receives a test order 516. The test order 516 may come from a laboratory information system. The test order 516 may also be received via a network or the computer system, or from a user or operator. The instrument manager 506 sends a set of control commands 508 to a transport device 512. The transport device 512 is adapted for conveying a biological sample between a pre-analytic apparatus 510 and an analyzer 514. The pre-analytic apparatus 510, the transport device 512 and the analyzer 514 are all adapted for sending device status 518, reports or information, to the sample workflow manager 502. The sample workflow manager 502 may be adapted for using the device status 518 for generating the pre-configured processing route 504. Also marked on the diagram is the group 520 which is the set of pre-analytic devices. In this embodiment the transport device 512 is considered to be part of the pre-analytic devices. In other embodiments, the transport device may be separate from the pre-analytic devices. Also marked on the diagram is the group 522. This is the set of all analysis system components. In this group is the pre-analytic apparatus 510, the transport device 512, and the analyzer 514.

Figure 6:
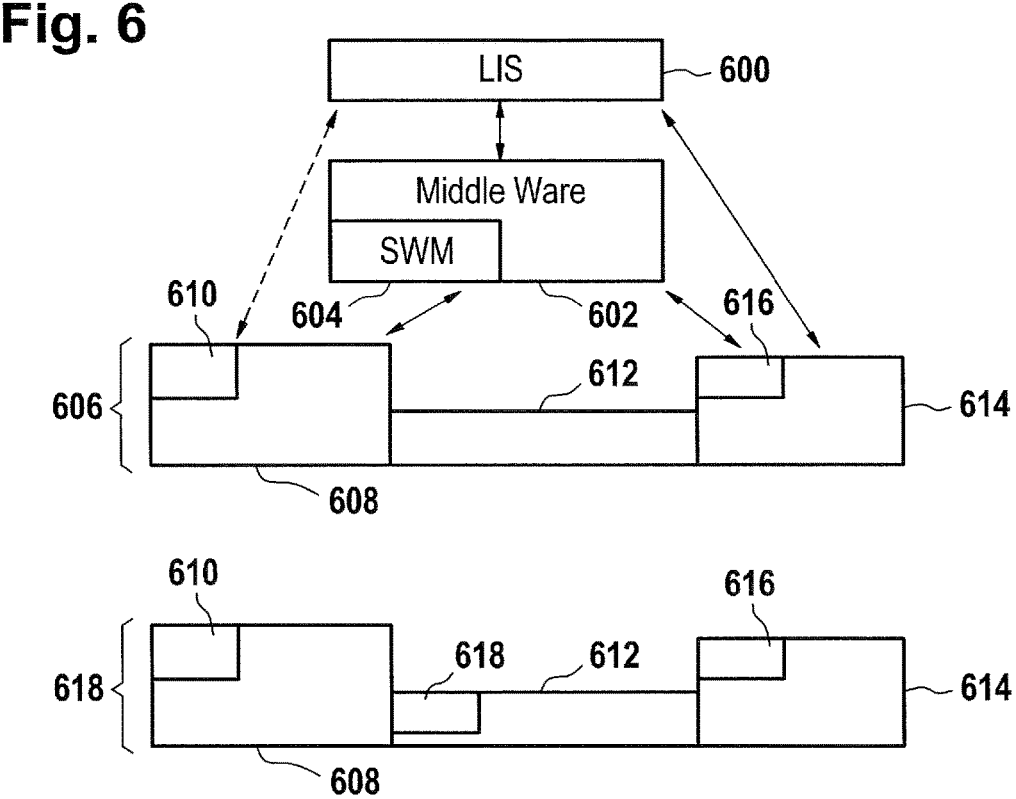
FIG. 6 illustrates an analysis system according to one or more embodiments shown and described herein.

FIG. 6 shows a further embodiment of an analysis system according to a further embodiment of the present disclosure. In this embodiment there is a laboratory information system 600 which is connected to a middleware system 602. A laboratory information system 600 as used herein encompasses a system which is able to manage the operation and functioning of a laboratory for performing the analysis of biological samples. The laboratory information system 600 may have a database of samples for which a test may be requested. A middleware system 602 as used herein encompasses a computer system or software program which is used to control multiple analytical systems together cooperatively. In this embodiment the sample workflow manager 604 is incorporated into the middleware system 602. In some embodiments there may be multiple sample workflow managers 604 incorporated into the middleware system 602. The laboratory information system 600 is networked to the middleware system 602. In some embodiments the laboratory information system 600 and the middleware system 602 may be implemented on the same computer system. In this embodiment, the middleware system 602 is known as being networked to a pre-analytic apparatus 608 and an analyzer 614. There is a transport device 612 for moving biological samples between the pre-analytic apparatus 608 and the analyzer 614. The pre-analytic apparatus 608 incorporates an instrument manager 610. Likewise the analyzer 614 also incorporates an instrument manager 616. The brackets 606 show and illustrate this first scenario wherein the pre-analytic apparatus 608 is shown as being connected or networked to the laboratory information system 600. The analyzer 614 is also shown as being networked or connected to the laboratory information system 600. In this way the laboratory information system 600 may receive device status 518, reports or information. Likewise the sample workflow manager 604 may also receive device status 518, reports or information. In the first scenario 606 the transport device 612 does not have an instrument manager. The brackets 618 show a second scenario which illustrates an alternative embodiment. In this alternative embodiment the transport device 612 also incorporates an instrument manager 618. In this embodiment the instrument manager 618 may also be able to send device status 518, reports or information to the middleware system 602 and/or the laboratory information system 600.

FIG. 7 illustrates an analysis system 700 according to a further embodiment of the present disclosure. The analysis system 700 shown is similar to the analysis system shown in FIG. 1. The analysis system 700 may be extended to any number of analysis system components. In the embodiment shown in FIG. 7, the instrument manager 104 has received a current process status 702. The current process status 702 may have been received as messages from the different analysis system components 106, 108, 110 or the instrument manager 104 may have polled the analysis system components 106, 108, 110 for their current operational status.

The computer-readable storage medium 162 of the instrument manager 104 is shown as containing multiple preconfigured processing routes 704. The preconfigured processing routes 704 were received from the sample workflow manager 102. The sample workflow manager 102 may for instance provide a number of preconfigured processing routes from its process route database 186. The computer-readable storage medium 162 is further shown as containing a set of selection rules 706 which may be used by a route selection module 708. The route selection module 708 is computer executable code stored in the computer-readable storage medium which uses the current process status 702 and/or the selection rules 706 to select a selected preconfigured processing route 710.

FIG. 8 shows a flow diagram which illustrates a method which may be performed using the analysis system 700 shown in FIG. 7. In a first step 800, the sample workflow manager 102 receives a process status 189. Next in step 802 the sample workflow manager 102 generates multiple preconfigured processing routes 704. The multiple preconfigured processing routes 704 may for instance be taken from the process route database 186. Next in step 804 the instrument manager 104 receives the multiple preconfigured processing routes 704 from the sample workflow manager 102.

Next in step 806, the instrument manager 104 receives a current process status 702. In some instances the current process status 702 may be identical with the process status 189 or the updated process status 193. In other instances the current process status may indicate a different operational status for the analysis system components 106, 108, 110. Next in step 808, preconfigured processing routes 704 which cannot be performed with the current process status 702 are eliminated from consideration. This prevents the sample workflow manager 102 from choosing a route which cannot be completed because a particular analysis system component is overloaded or is currently not functioning. Next 810, one of the multiple preconfigured processing routes 704 is selected using selection rules 706. Next in step 812, the instrument manager 104 generates commands using the command generation module 170 and the selected preconfigured processing route 710. Finally in step 814 the biological sample 114 is transported to a sequence of analysis system components using the commands that were just generated.

The method illustrated in FIG. 8 may be performed by a suitably programmed computer or controller. A program or machine executable instructions for performing the method may be stored on one or more non-transitory computer readable storage mediums.

The present invention is not to be limited in scope by the specific embodiments described herein. Indeed, various modifications of the present invention, in addition to those described herein, will be apparent to those skilled in the art from the foregoing description and accompanying drawings. Thus, such modification are intended to fall within the scope of the appended claims. Additionally, various references are cited throughout the specification, the disclosures of which are each incorporated herein by reference in their entirety.

What is claimed is:

1. An analysis system for analyzing a biological sample comprising:
an instrument manager;
at least first and second analysis system components configured to perform an analysis, wherein the first analysis system component comprises a transport device, and the second analysis system component comprises at least one of a pre-analytic device, an analyzer and a post-analytic device configured to characterize a property of the biological sample, the second analysis system component also comprises a pipetter configured to add chemicals to the biological sample, and an embedded controller communicatively coupled to the instrument manager;
a sample workflow manager communicatively coupled to the instrument manager, wherein the sample workflow manager is communicatively coupled to the at least first and second analysis system components and is configured to receive a process status from the at least first and second analysis system components, wherein the sample workflow manager is configured to provide at least one preconfigured processing route to the instrument manager in accordance with the process status;
wherein the instrument manager is communicatively coupled to the transport device;

wherein the instrument manager comprises a memory configured to store the at least one preconfigured processing route received from the sample workflow manager and at least one additional preconfigured processing route, wherein the instrument manager is configured to receive a test order and to analyze the biological sample using the second analysis system component in accordance to the test order, wherein the instrument manager is configured to generate commands to control the transport device which is arranged to physically transport the biological sample to the second analysis system component in accordance with the test order and the at least one preconfigured processing route, and to switch to the at least one additional preconfigured processing route when a failure is detected by the instrument manager with regard to the at least one preconfigured processing route when the test order is executed by the instrument manager;

wherein the instrument manager is configured to determine, based on a selection rule set, when to retest the biological sample by a different analysis system component and to compare results; and wherein the transport device is arranged to physically move a sample holder containing the biological sample into a switching unit, in which the switching unit is arranged to change a direction of movement of the biological sample along the transport device upon leaving the switching unit, and in which the change in the direction of the movement of the biological sample along the transport device upon leaving the switching unit depends on the selection rule set and the component of the analysis system to which the sample is moved by the transport device.

2. The analysis system of claim 1, wherein the at least one additional preconfigured processing route is a plurality of additional preconfigured processing routes, and the instrument manager is configured to select a preconfigured processing route from among the plurality of additional preconfigured processing routes such that all tests requested by the test order are satisfied.

3. The analysis system of claim 1, wherein the instrument manager is configured to receive the process status from the at least first and second analysis system components, wherein the at least one additional preconfigured processing route is a plurality of additional preconfigured processing routes, and the instrument manager is configured to select a preconfigured processing route from among the plurality of additional preconfigured processing routes at least partially by determining which of the plurality of additional preconfigured processing routes is allowed by the process status.

4. The analysis system of claim 1, wherein the at least one additional preconfigured processing route is a plurality of additional preconfigured processing routes, and the instrument manager is configured to select a preconfigured processing route from among the plurality of additional preconfigured processing routes at least partially in accordance with the selection rule set.

5. The analysis system of claim 1 further comprising a centrifuge configured to centrifuge the biological sample.

6. The analysis system of claim 1 wherein the second analysis system component is configured to add an enzyme to the biological sample.

7. The analysis system of claim 1 wherein the workflow manager is configured to:
detect that the biological sample is measured to be outside of a range; and
send a query from the workflow manager upon.

8. The analysis system of claim 1, wherein the post-analytic device is further configured to cap the biological sample for storage.

9. The analysis system of claim 1, wherein the instrument manager is configured to select an analysis system component with a lower workload based upon the selection rule set.

10. A method for analyzing a biological sample comprising:
providing an analysis system comprising:
a sample workflow manager;
an instrument manager coupled communicatively to the sample workflow manager; and
at least first and second analysis system components performing an analysis, wherein the first analysis system component comprises a transport device, and the second analysis system component comprises:
at least one of a pre-analytic device, an analyzer and a post-analytic device that characterizes a property of the biological sample,
a pipetter for adding chemicals to the biological sample, and
an embedded controller communicating with the instrument manage,
wherein the sample workflow manager is communicatively coupled to the at least first and second analysis system components and receives a process status from the at least first and second analysis system components,
wherein the sample workflow manager provides at least one preconfigured processing route to the instrument manager in accordance with the process status,
wherein the instrument manager is communicatively coupled to the transport device;
wherein the instrument manager comprises a memory storing the at least one preconfigured processing route received from the sample workflow manager and at least one additional preconfigured processing route,
wherein the instrument manager receives a test order and analyzes the biological sample using the second analysis system component,
wherein the instrument manager generates commands to control the transport device, which physically transports the biological sample to the second analysis system component in accordance with the test order and the at least one preconfigured processing route, and to switch to the at least one additional preconfigured processing route when a failure is detected by the instrument manager with regard to the at least one preconfigured processing route when executing the test order,
wherein the instrument manager determines, based on a selection rule set, when to retest the biological sample by a different analysis system component and to compare results,
wherein the transport device physically moves a sample holder containing the biological sample into a switching unit, which changes a direction of movement of the biological sample along the transport device upon leaving the switching unit, the direction varying depending on the selection rule set and the component of the analysis system to which the sample is moved;
receiving by the sample workflow manager the process status from the at least first and second analysis system components;
providing via the sample workflow manager the at least one preconfigured processing route to the instrument manager in accordance with the process status;

controlling the transport device via the instrument manager in accordance with the test order and the at least one preconfigured processing route;

moving, via the transport device, the sample holder containing the biological sample into the switching unit; and changing the direction of movement of the biological sample along the transport device upon leaving the switching unit based on the selection rule set and the component of the analysis system to which the sample is being moved by the transport device.

11. The method of claim 10, wherein the at least one additional preconfigured processing route is a plurality of additional preconfigured processing routes, and the instrument manager selects a preconfigured processing route from among the plurality of additional preconfigured processing routes such that all tests requested by the test order are satisfied.

12. The method of claim 10, wherein the at least one additional preconfigured processing route is a plurality of additional preconfigured processing routes, and the instrument manager selects a preconfigured processing route from among the plurality of additional preconfigured processing routes at least partially in accordance with the selection rule set.

13. The method of claim 10, further comprising centrifuging the biological sample.

14. The method of claim 10 wherein the second analysis system component adds an enzyme to the biological sample.

15. The method of claim 10 further comprising:
detecting that the biological sample is measured to be outside of a range; and
sending a query from the workflow manager upon.

16. The method of claim 10 further comprising capping the biological sample for storage.

17. The method of claim 10 further comprising specifying selection of an analysis system component with a lower workload based upon the selection rule set.

18. The method according to claim 10, further comprising switching to the at least one additional preconfigured processing route due to a failure being detected by the instrument manager with regard to the at least one preconfigured processing route.

19. The method according to claim 10, further comprising:
determining, based on the selection rule set, a retest of the biological sample by a different analysis system component; and
comparing results of the retest from the different analysis component with the analysis performed by the second analysis system component.

* * * * *

UNITED STATES PATENT AND TRADEMARK OFFICE
CERTIFICATE OF CORRECTION

Page 1 of 1

PATENT NO. : 10,197,584 B2
APPLICATION NO. : 13/288416
DATED : February 5, 2019
INVENTOR(S) : Andrzej Knafel and Joerg Haechler It is certified that error appears in the above-identified patent and that said Letters Patent is hereby corrected as shown below:

In the Drawings

In sheet 7, figure 8, (804), delete "recieves" and insert --receives--, therefor.

In sheet 7, figure 8, (808), delete "eliminted" and insert --eliminated--, therefor.

In the Claims

In Column 18, Claim 10, Line 23, delete "manage" and insert --manager--, therefor.

Signed and Sealed this
Nineteenth Day of November, 2019

Andrei Iancu
*Director of the United States Patent and Trademark Office*